(12) United States Patent
Miller et al.

(10) Patent No.: US 11,883,318 B2
(45) Date of Patent: *Jan. 30, 2024

(54) MENSTRUAL CUP

(71) Applicant: The Flex Company, Venice, CA (US)

(72) Inventors: Andrew Ross Miller, Venice, CA (US);
Jane Hartman Adamé, Venice, CA (US); Brittney Seel, Venice, CA (US);
Lauren Schulte Wang, Venice, CA (US)

(73) Assignee: The Flex Company, Venice, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/511,488

(22) Filed: Oct. 26, 2021

(65) Prior Publication Data

US 2022/0047411 A1    Feb. 17, 2022

Related U.S. Application Data

(63) Continuation of application No. 17/090,796, filed on Nov. 5, 2020, now Pat. No. 11,154,416.

(60) Provisional application No. 62/930,804, filed on Nov. 5, 2019.

(51) Int. Cl.
*A61F 5/455* (2006.01)
*A61F 5/451* (2006.01)

(52) U.S. Cl.
CPC ............ *A61F 5/4553* (2013.01); *A61F 5/455* (2013.01); *A61F 5/451* (2013.01)

(58) Field of Classification Search
CPC ......... A61F 5/451; A61F 5/455; A61F 5/4553
See application file for complete search history.

(56) References Cited

U.S. PATENT DOCUMENTS

| | | | |
|---|---|---|---|
| 1,634,555 A | | 7/1927 | Peloubet |
| 1,891,761 A | * | 12/1932 | Goodard ............... A61F 5/4553 |
| | | | 604/330 |
| 1,996,242 A | * | 4/1935 | Hagedorn ............. A61F 5/4553 |
| | | | 604/330 |
| 2,061,384 A | * | 11/1936 | Manegold ............. A61F 5/4553 |
| | | | 604/330 |
| 2,089,113 A | * | 8/1937 | Chalmers ............... A61F 5/4553 |
| | | | D24/141 |

(Continued)

FOREIGN PATENT DOCUMENTS

| | | |
|---|---|---|
| GB | 2 425 260 A | 10/2006 |
| TW | 201914552 A | 4/2019 |

(Continued)

OTHER PUBLICATIONS https://www.tencel.com/sustainability; TENCEL "Sustainability—TENCEL fibers help maintain environmental balance by being integrated into nature's cycle"; 7 pages.

(Continued)

*Primary Examiner* — Guy K Townsend
(74) *Attorney, Agent, or Firm* — Haynes and Boone, LLP

(57) ABSTRACT

A menstrual device with a reservoir portion attached to a rim portion where the rim of the device is configured to improve use and comfort. The edge of the reservoir portion may be molded into the defined geometry of the rim portions. Additionally, the rim may have one or more channels and/or elements positioned within the defined geometry of the rim.

5 Claims, 19 Drawing Sheets

(56) References Cited

U.S. PATENT DOCUMENTS

| | | | | |
|---|---|---|---|---|
| RE21,943 E | * | 11/1941 | Munro | A61F 5/4553 604/285 |
| 2,321,340 A | * | 6/1943 | Waterbury | B29C 70/70 264/294 |
| 2,534,900 A | * | 12/1950 | Chalmers | A61F 5/4553 604/330 |
| 2,616,426 A | * | 11/1952 | Gordon | A61F 5/4553 604/330 |
| 2,845,071 A | | 7/1958 | Wade | |
| 3,128,767 A | * | 4/1964 | Nolan | A61F 6/08 604/330 |
| 3,157,180 A | * | 11/1964 | Bakunin | A61F 5/4553 604/330 |
| 3,216,422 A | * | 11/1965 | Steiger | A61F 6/08 604/330 |
| 3,404,682 A | * | 10/1968 | Waldron | A61F 13/26 128/838 |
| 3,528,423 A | | 9/1970 | Lee | |
| 3,595,236 A | | 7/1971 | Appleton et al. | |
| 3,626,942 A | * | 12/1971 | Waldron | A61F 6/08 604/330 |
| 3,841,333 A | * | 10/1974 | Zalucki | A61F 5/4553 604/330 |
| 3,845,766 A | * | 11/1974 | Zoller | A61F 5/4553 D24/141 |
| 4,246,901 A | | 1/1981 | Frosch | |
| 4,381,771 A | * | 5/1983 | Gabbay | A61F 6/08 128/836 |
| 4,486,191 A | | 12/1984 | Jacob | |
| 4,496,355 A | | 1/1985 | Hall et al. | |
| 4,785,804 A | * | 11/1988 | Tlapek | A61F 6/08 128/841 |
| 4,799,929 A | * | 1/1989 | Knowles | A61F 5/4553 604/331 |
| 4,810,247 A | | 3/1989 | Glassman | |
| 4,848,363 A | * | 7/1989 | Cattanach | A61F 5/4553 128/834 |
| 4,889,533 A | * | 12/1989 | Beecher | A61F 5/4407 604/355 |
| 4,961,436 A | * | 10/1990 | Koch | A61F 6/08 128/834 |
| D323,212 S | * | 1/1992 | Crawford | D24/141 |
| 5,295,984 A | * | 3/1994 | Contente | A61F 5/4553 604/327 |
| 5,342,331 A | * | 8/1994 | Silber | A61F 13/34 604/385.18 |
| 5,476,455 A | * | 12/1995 | Silber | A61F 13/34 604/330 |
| 5,498,252 A | | 3/1996 | Silber | |
| 5,827,248 A | * | 10/1998 | Crawford | A61F 5/4553 604/328 |
| 5,928,249 A | * | 7/1999 | Saadat | A61B 17/42 606/119 |
| 5,947,992 A | * | 9/1999 | Zadini | A61F 5/4553 606/191 |
| 6,126,616 A | * | 10/2000 | Sanyal | A61B 10/0291 128/834 |
| 6,168,609 B1 | * | 1/2001 | Kamen | A61F 5/4553 600/573 |
| 6,241,846 B1 | * | 6/2001 | Contente | B29C 66/114 156/379 |
| 6,264,638 B1 | * | 7/2001 | Contente | A61M 31/002 604/285 |
| 6,332,878 B1 | * | 12/2001 | Wray | A61F 6/08 128/830 |
| 6,796,973 B1 | * | 9/2004 | Contente | A61F 5/4553 128/832 |
| 7,845,355 B2 | * | 12/2010 | Moench | A61F 6/08 128/833 |
| 8,282,612 B1 | | 10/2012 | Miller | |
| 8,454,493 B2 | * | 6/2013 | La Vean | A61F 6/08 600/33 |
| 8,690,847 B2 | * | 4/2014 | Norman | A61F 5/4553 604/327 |
| 8,795,248 B2 | * | 8/2014 | Shihata | A61F 5/4553 604/385.18 |
| 9,357,982 B2 | * | 6/2016 | Edmunds | A61F 13/2045 |
| 9,827,136 B2 | | 11/2017 | Shaviv | |
| 9,993,371 B2 | | 6/2018 | Kasper | |
| 10,016,308 B2 | * | 7/2018 | Knox | A61F 13/00085 |
| 10,188,543 B2 | * | 1/2019 | Lin | A61F 5/4405 |
| D852,361 S | * | 6/2019 | Sedic | D24/141 |
| D852,362 S | * | 6/2019 | Sedic | D24/141 |
| 10,357,395 B2 | * | 7/2019 | Miller | A61F 5/4404 |
| D864,390 S | * | 10/2019 | Sedic | D24/141 |
| 10,470,920 B1 | * | 11/2019 | Vasudeva | A61F 5/4553 |
| 10,582,913 B2 | * | 3/2020 | Ealovega | A61F 5/4553 |
| D892,324 S | * | 8/2020 | Yi | A61F 13/34 D24/141 |
| D894,386 S | * | 8/2020 | LeClerc | A61F 5/4407 D24/141 |
| D895,798 S | * | 9/2020 | Newman | A61F 6/08 D24/141 |
| D895,799 S | * | 9/2020 | Newman | A61F 6/08 D24/141 |
| D895,800 S | * | 9/2020 | Knox | D24/141 |
| 10,898,368 B2 | * | 1/2021 | Medas | A61F 5/4553 |
| 10,959,873 B2 | * | 3/2021 | Wilson | A61F 5/4553 |
| 11,000,402 B2 | * | 5/2021 | Park | A61F 5/448 |
| 11,013,633 B2 | * | 5/2021 | Pitacco | A61F 5/4553 |
| 11,045,246 B1 | * | 6/2021 | Schwartz | A61F 5/4553 |
| 11,076,980 B2 | * | 8/2021 | Hu | A61F 5/4553 |
| 11,096,819 B2 | * | 8/2021 | Brown | A61F 5/4553 |
| 11,154,416 B2 | * | 10/2021 | Miller | A61F 5/4553 |
| 11,234,857 B2 | * | 2/2022 | Miller | A61F 5/4553 |
| 11,291,535 B2 | * | 4/2022 | Conti | A61B 10/0012 |
| 11,324,628 B2 | * | 5/2022 | Bauer | A61F 5/4553 |
| 11,369,509 B2 | * | 6/2022 | Garriga I Rodo | A61F 6/12 |
| 11,484,433 B1 | * | 11/2022 | Miller | A61F 5/4553 |
| 11,534,329 B1 | * | 12/2022 | Thornton | A61F 5/4404 |
| 11,583,433 B2 | * | 2/2023 | Brush | A61F 5/4553 |
| 2001/0018577 A1 | * | 8/2001 | Fitzpatrick | A61F 5/4553 604/328 |
| 2006/0260619 A1 | * | 11/2006 | Moench | A61F 6/08 128/837 |
| 2008/0077097 A1 | * | 3/2008 | Chambers | A61F 5/4553 604/330 |
| 2008/0200888 A1 | * | 8/2008 | Gooch | A61F 5/4553 604/330 |
| 2010/0242968 A1 | * | 9/2010 | Vean | A61F 6/08 128/830 |
| 2010/0312204 A1 | * | 12/2010 | Sheu | A61F 5/4408 604/330 |
| 2011/0094519 A1 | | 4/2011 | Gopal et al. | |
| 2013/0110060 A1 | * | 5/2013 | Shihata | A61F 5/4553 604/330 |
| 2013/0138135 A1 | * | 5/2013 | Rosen | A61B 17/12 606/197 |
| 2014/0012216 A1 | | 1/2014 | Shaviv | |
| 2015/0164680 A1 | * | 6/2015 | Chen | A61F 13/8405 604/359 |
| 2015/0202076 A1 | | 7/2015 | Wijzen | |
| 2016/0278988 A1 | * | 9/2016 | Knox | A61F 15/005 |
| 2016/0361208 A1 | | 12/2016 | Kasper | |
| 2017/0189222 A1 | * | 7/2017 | Lin | A61F 5/4553 |
| 2017/0325788 A1 | * | 11/2017 | Ealovega | A61F 5/4553 |
| 2017/0360594 A1 | * | 12/2017 | Park | A61F 5/449 |
| 2018/0028350 A1 | * | 2/2018 | Wilson | A61F 5/4553 |
| 2018/0199874 A1 | * | 7/2018 | Hwang | A61B 10/0045 |
| 2018/0214298 A1 | * | 8/2018 | Medas | A61F 5/4553 |
| 2018/0338779 A1 | * | 11/2018 | Haeri | A61B 17/425 |
| 2019/0021898 A1 | * | 1/2019 | Ahn | A61F 5/4553 |
| 2019/0083296 A1 | * | 3/2019 | Miller | A61F 5/4553 |
| 2019/0125571 A1 | * | 5/2019 | Hu | A61F 5/4553 |
| 2019/0151136 A1 | * | 5/2019 | Garriga I Rodo | A61F 5/4553 |
| 2019/0282350 A1 | * | 9/2019 | Conti | A61B 10/0045 |
| 2019/0314191 A1 | * | 10/2019 | Bobarikin | A61F 5/4553 |
| 2019/0336167 A1 | * | 11/2019 | La Vean | A61B 17/425 |
| 2019/0336318 A1 | * | 11/2019 | Kubo | A61F 5/455 |
| 2019/0358077 A1 | * | 11/2019 | Bauer | A61F 5/4553 |

(56) References Cited

U.S. PATENT DOCUMENTS

| | | | |
|---|---|---|---|
| 2020/0046572 A1* | 2/2020 | Hwang | A61F 5/4404 |
| 2020/0060864 A1* | 2/2020 | Font Caselles | A61F 5/4408 |
| 2020/0060865 A1* | 2/2020 | Hwang | A61F 5/4553 |
| 2020/0078208 A1* | 3/2020 | Stoebe-Latham | A61F 5/4553 |
| 2020/0078209 A1* | 3/2020 | Stoebe-Latham | A61F 13/55105 |
| 2020/0113500 A1* | 4/2020 | Hwang | G01N 33/49 |
| 2020/0179157 A1* | 6/2020 | Pitacco | A61F 5/44 |
| 2020/0197232 A1* | 6/2020 | Tokunaga | A61F 13/4756 |
| 2020/0206019 A1* | 7/2020 | Brown | A61F 5/4553 |
| 2020/0214876 A1* | 7/2020 | Tsai | A61F 5/4553 |
| 2020/0323519 A1* | 10/2020 | Ealovega | A61F 5/4553 |
| 2020/0368059 A1* | 11/2020 | Greb | A61F 5/4553 |
| 2020/0375788 A1* | 12/2020 | Zhang | A61F 5/4553 |
| 2021/0113363 A1* | 4/2021 | Evans | A61F 5/4553 |
| 2021/0128342 A1* | 5/2021 | Miller | A61F 5/4553 |
| 2021/0267788 A1* | 9/2021 | Ramos | A61F 5/4407 |
| 2021/0330369 A1* | 10/2021 | Schwartz | A61B 1/307 |
| 2021/0338474 A1* | 11/2021 | Mamo | A61F 5/4553 |
| 2022/0047411 A1* | 2/2022 | Miller | A61F 5/4553 |
| 2022/0133525 A1* | 5/2022 | Martz | A61F 5/4553 604/330 |
| 2022/0183812 A1* | 6/2022 | Conti | A61F 2/005 |
| 2022/0331146 A1* | 10/2022 | Brush | A61F 5/4553 |
| 2022/0331147 A1* | 10/2022 | Brush | A61F 5/4553 |
| 2022/0331148 A1* | 10/2022 | Miller | A61F 5/4404 |
| 2022/0370239 A1* | 11/2022 | Smullin | A61F 5/4553 |
| 2022/0409423 A1* | 12/2022 | Priya | A61F 5/451 |
| 2023/0016976 A1* | 1/2023 | Miller | A61F 5/4553 |
| 2023/0149204 A1* | 5/2023 | Thornton | A61F 5/4553 604/330 |

FOREIGN PATENT DOCUMENTS

| | | |
|---|---|---|
| WO | 02080827 A1 | 10/2002 |
| WO | 2007082341 A1 | 7/2007 |
| WO | 2015012776 A1 | 1/2015 |
| WO | 2018178887 A1 | 10/2018 |
| WO | 2019055855 A1 | 3/2019 |
| WO | 2019221382 A1 | 11/2019 |

OTHER PUBLICATIONS https://en.wikipedia.org/wiki/Viscose "Viscose" definition; 3 pages.
Ed Mass; "Eco-Fiber or Fraud? Are Rayon, Modal, and Tencel Environmental Friends or Foes?" Natural Life Magazine; editor's blog; 6 pages.
PCT/US2020/059204 International Search Report and Written Opinion; dated Feb. 4, 2021; 11 pages.
PCT/US2018/051187 International Search Report and Written Opinion; dated Feb. 25, 2019; 15 pages.

* cited by examiner

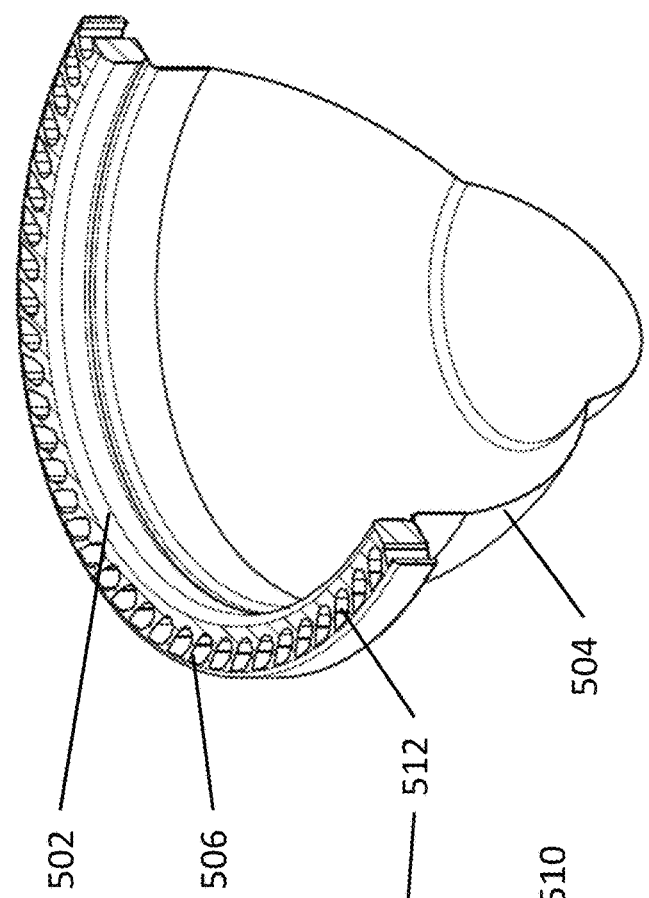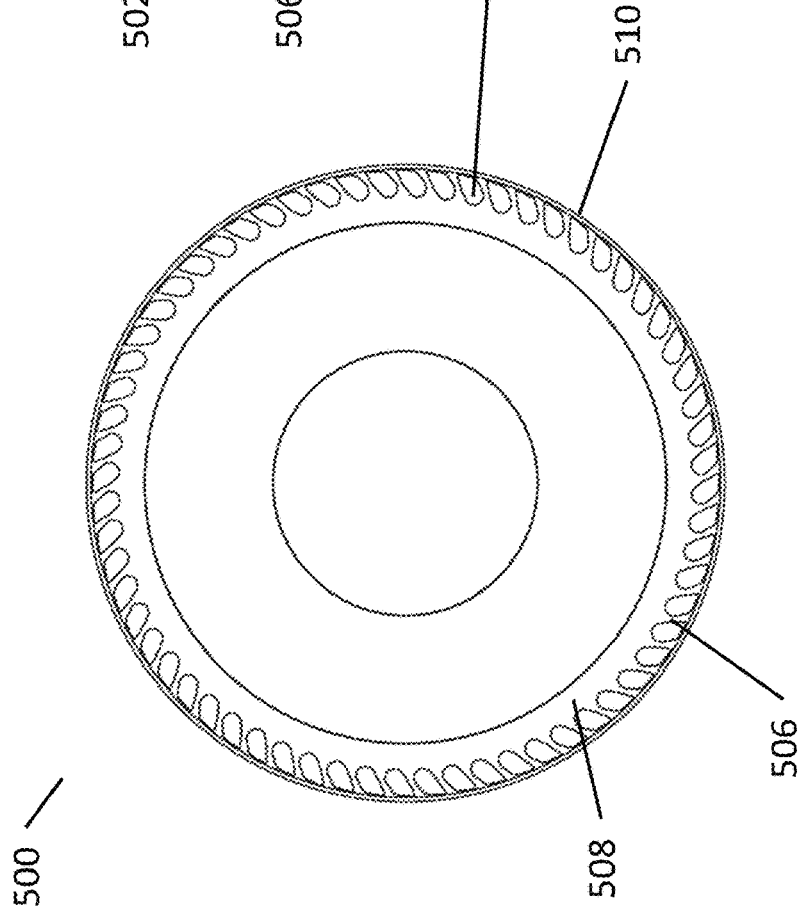

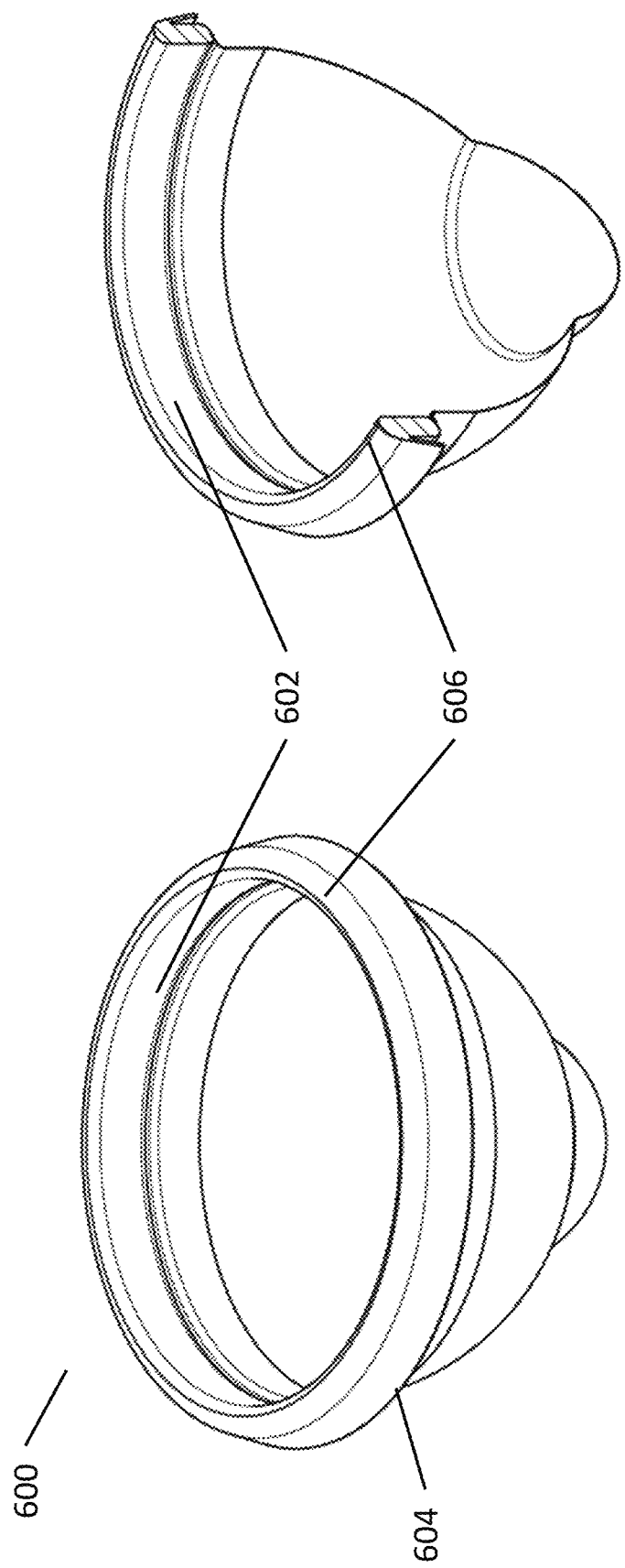

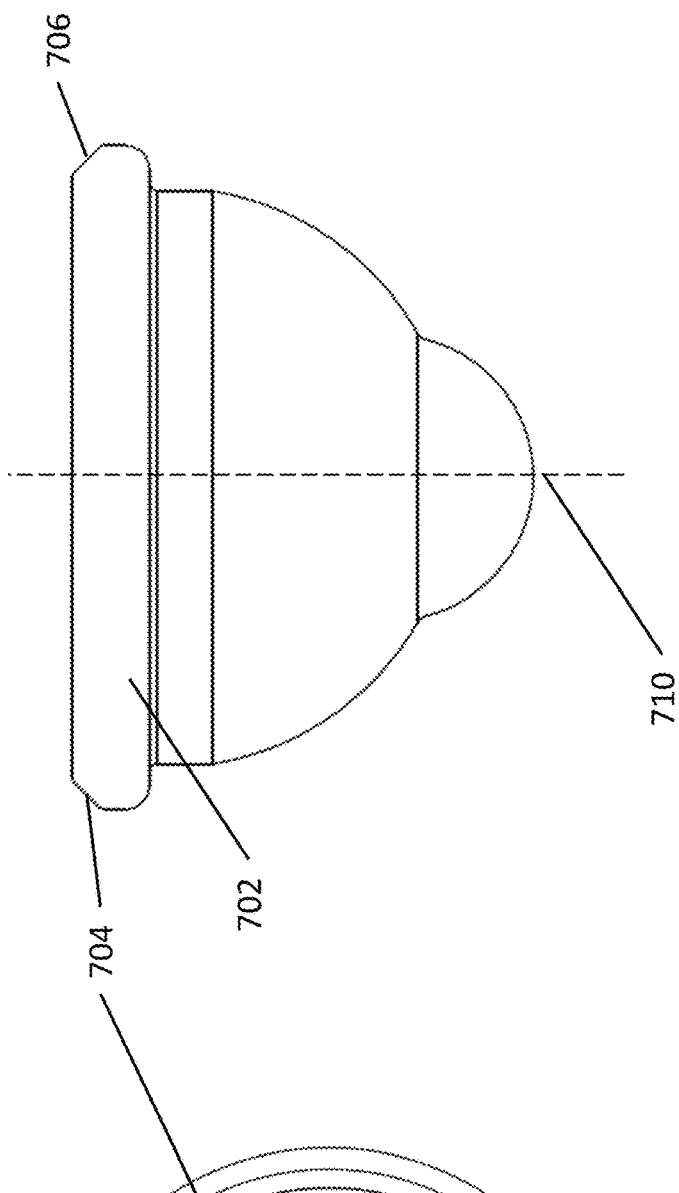
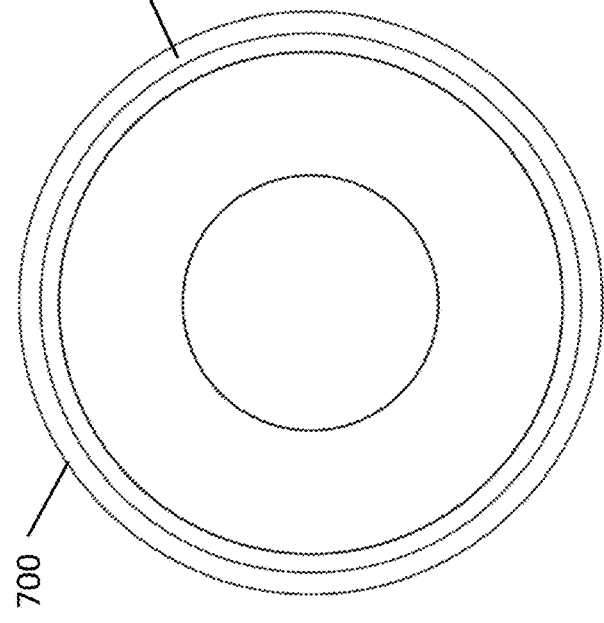

| Concept | Image | Description | Volume |
|---|---|---|---|
| Nominal |  | Half Circle | 0.368 in^3 |
| A |  | Triangular profile | 0.260 in^3 |
| B |  | U shape profile | 0.256 in^3 |
| C |  | Shorter rim height | 0.219 in^3 |
Fig. 8

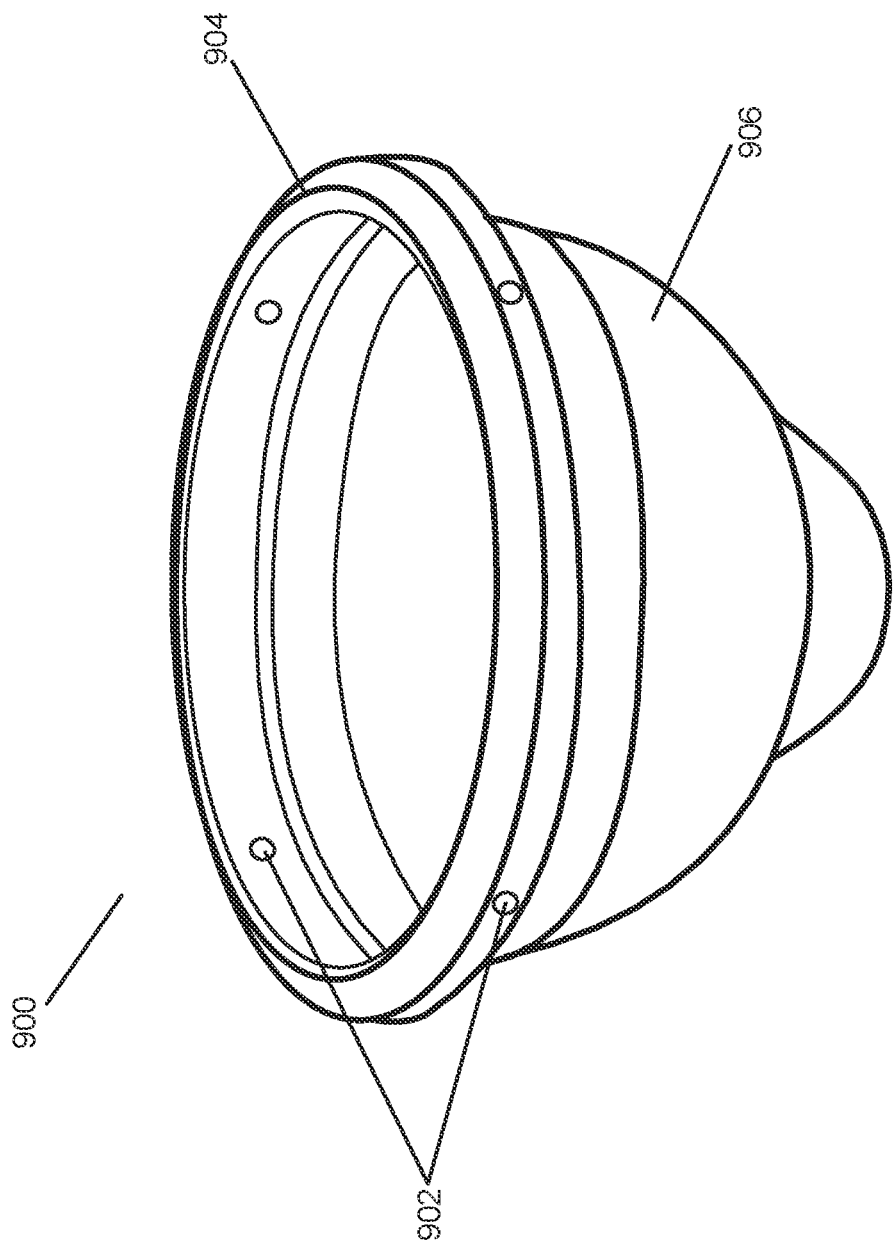

MENSTRUAL CUP

CROSS-REFERENCED APPLICATIONS

This application is a continuation of U.S. patent application Ser. No. 17/090,796, filed Nov. 5, 2020, which claims priority to U.S. Provisional Application 62/930,804, all of which are included herein by reference in their entirety.

FIELD OF THE INVENTION

The present invention generally relates to menstrual collection devices, specifically menstrual discs and/or menstrual cups.

BACKGROUND OF THE INVENTION

A person who menstruates will typically use a tampon or pad to absorb catamenial fluids. Alternatives to tampons and pads exist to collect catamenial fluids such as menstrual cups and/or menstrual discs. Menstrual cups have been in use and have been known as is described further in U.S. Pat. No. 1,891,761 to Goddard, U.S. Pat. No. 1,996,242 to Hagedom, U.S. Pat. No. 2,089,113 to Chalmers, U.S. Pat. No. 5,827,248 to Crawford, and U.S. Design Pat. No. D323,212 to Crawford. Such devices are commonly used as a replacement to other catamenial devices such as tampons and sanitary napkins.

The typical menstrual cup is a cup like device with a reservoir or catchment area and a rim designed to be inserted into the vagina and catch menses. Goddard, Hagedome, and Chalmers devices are worn in a lower region of the vaginal canal where there are more nerve endings. These menstrual cups form a vacuum seal with the vaginal wall that must be disrupted before the cup is removed.

An alternative class of menstrual cups is disclosed in U.S. Pat. No. 5,292,984 to Potter. Similar to the menstrual cups of Goddard, Hagedome, and Chalmers, the Potter device is designed to be foldable such that it can be inserted into the vagina and then expand once in position. However, the Potter device is designed to sit in the fornix, an anatomical region around the cervix at the top of the vaginal canal where there are fewer nerve endings. Often times this type of menstrual cup is referred to as a menstrual disc. Menstrual discs may be constructed of materials that are single-use or from materials that are reusable. Accordingly, many manufactured follow traditional methods of manufacture to produce resilient type devices for ease of insertion and use. However, with an increased interest in protecting the environment, with more sustainable and/or biodegradable products, many manufactures fail to take advantage of improved technologies in the design and manufacture of menstrual products.

BRIEF SUMMARY OF THE INVENTION

Many embodiments are directed to menstrual cups and/or discs, specifically the design and manufacture of said devices that allow for improved user experience with insertion and removal as well as the use of more sustainable materials. Many embodiments include a body portion having an exterior surface and an interior surface wherein the interior surface defines a reservoir and where the body portion has a defined outer edge with a first diameter. The cup also has a resiliently foldable rim with defined dimensions of height, width, and diameter, wherein the diameter of the rim is equal to or greater than the first diameter of the body portion, and wherein the height of the rim is defined by an upper edge and a lower edge and the width of the rim is defined by a thickness of the rim that extends between an outward surface to an inward surface. The resiliently foldable rim has a chamfered leading edge wherein the chamfered leading edge is defined by a sloped surface extending downward at angle off axis from the upper edge and extending to a point along the outward surface below the upper edge.

In other embodiments, the cup has at least one protrusion extending outward from the outer edge of the rim and circumferentially disposed around the rim wherein the protrusion is configured to be resiliently foldable and compliant so as to comply with the resiliently foldable rim and wherein the at least one protrusion is configured to contact a portion of the user's body and form a seal.

In still other embodiments, the at least one protrusion extends outward at a downward angle away from the resiliently foldable rim.

In yet other embodiments, the cup has a plurality of protrusions having an elongated body with a first end and a second end where the first end is connected to an inner portion of the resiliently foldable rim and extends outward towards the outer surface and connects to an inward portion of the outward surface, such that each of the plurality of protrusions make up a portion of the resiliently foldable rim and wherein each of the plurality of protrusions are individually disposed on the inner portion of the rim in a circumferential pattern.

In still yet other embodiments, each of the plurality of protrusions have at least a portion thereof near the first end that overlaps at least a portion of an adjacent protrusion.

In other embodiments, each of the plurality of protrusions are disposed at a helical angle with respect to the outer surface of the rim.

In still other embodiments, the cup has a plurality of channels disposed in the resiliently foldable rim wherein each of the plurality of channels extend through at least a portion of the resiliently foldable rim.

In yet other embodiments, the plurality of channels extend horizontally from an interior surface of the rim to an exterior surface of the rim.

In still yet other embodiments, the plurality of channels extend at an angle that is off axis from the vertical and wherein the angle extends from an inner surface towards and outer surface.

In other embodiments, the plurality of channels extend at an angle that is off axis from the vertical and wherein the angle extends from an outer surface towards and inner surface.

In still other embodiments, the cross section of the channel is a "C" cross section.

In yet other embodiments, the plurality of channels are disposed near an outer edge of the resiliently foldable rim and form a cutout of the rim.

In still yet other embodiments, the plurality of channels are disposed near an inner edge of the resiliently foldable rim and form a cutout of the rim.

In other embodiments, the resiliently foldable rim has a cross section selected from a group consisting of triangular, half circular, and U shaped.

In still other embodiments, the body portion of the cup has a volume ranging from 25 ml to 75 ml.

In yet other embodiments, the rim is molded onto the body portion of the cup such that the rim encloses the defined outer edge of the body portion.

In still yet other embodiments, the rim and the body portion are made of materials of different durometers.

Other embodiments are directed to a menstrual cup that includes a body portion having an exterior surface and an interior surface wherein the interior surface defines a reservoir and wherein the body portion has a defined outer edge with a first diameter. The cup has a resiliently foldable rim having defined dimensions of height, width, and diameter, wherein the diameter of the rim is equal to or greater than the first diameter of the body portion, and wherein the height of the rim is defined by an upper edge and a lower edge and the width of the rim is defined by a thickness of the rim that extends between an outward surface to an inward surface. Additionally the resiliently foldable rim has a contoured leading edge.

In still other embodiments, the contoured leading edge is defined by a sloped surface extending downward at an angle off axis from the upper edge and extending to a point along the outward surface below the upper edge.

In yet other embodiments, the of axis angle is equal to 45°.

In still yet other embodiments, the contoured leading edge is defined by a curved surface extending from the upper edge down towards the lower edge and to a point along the outward surface.

Other embodiments are directed to a menstrual cup with a body portion having an exterior surface and an interior surface wherein the interior surface defines a reservoir and wherein the body portion has a defined outer edge with a first diameter. The cup has a resiliently foldable rim having defined dimensions of height, width, and diameter, wherein the diameter of the rim is equal to or greater than the first diameter of the body portion. The height of the rim is defined by an upper edge and a lower edge and the width of the rim is defined by a thickness of the rim that extends between an outward surface to an inward surface. The body portion of the cup attaches to the rim between the upper edge and lower edge and on the inner diameter.

Other embodiments are directed to a menstrual cup with a body portion having an exterior surface and an interior surface wherein the interior surface defines a reservoir and wherein the body portion has a defined outer edge with a first diameter. The cup has a resiliently foldable rim having defined dimensions of height, width, and diameter, wherein the diameter of the rim is equal to or greater than the first diameter of the body portion. The height of the rim is defined by an upper edge and a lower edge and the width of the rim is defined by a thickness of the rim that extends between an outward surface to an inward surface. The rim also has one or more channels transecting the height of the rim where the cross section of each of the one or more channels is a circular cross section.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein:

FIGS. 5A through 5C a menstrual device with a resiliently compliant rim element in accordance with embodiments of the invention.

FIGS. 6A through 6C illustrate a menstrual device with a circumferential protrusion on an outer surface of the rim in accordance with embodiments of the invention.

FIGS. 7A through 7E illustrate a menstrual device with a contoured leading edge in accordance with embodiments of the invention.

FIG. 8 is a tabular illustration of various rim cross sections in accordance with several embodiments of the invention.

FIGS. 9A through 9H illustrate menstrual devices with device removal mechanisms in accordance with several embodiments of the invention.

DETAILED DESCRIPTION OF THE INVENTION

Turning now to the drawings, systems and methods of a menstrual cup and/or disc are described. In many embodiments of the invention, the menstrual device contains a resilient rim connected to a reservoir portion where the rim and reservoir are foldable such that it can be folded and inserted into a vaginal canal. Additionally, many embodiments incorporate a rim material that is different from the reservoir material and the reservoir material is overmolded onto the rim such that the reservoir is enclosed at its edge by the rim material. Many embodiments may also include air equalization pathways to improve the removal process of the device.

Menstrual cups, as previously described, have been in use and are well known in the field of menstrual devices. However, known menstrual cups have many disadvantages. The ease of insertion and removal can present certain difficulties that may lead users to resort to less ideal methods of collection. For example, known cups generally lack a function to aid in the removal of the cup, having only a small gripped stem which when pulled and due to the seal formed between the cup and the vagina creates a mechanical suction force between the cup and the vagina and cervix prohibiting, not aiding, removal. Additionally, some menstrual cups similar to the Porter design have no ideal method of removal. Furthermore, traditional cups can be difficult to insert. Existing cups are inserted with specific fold techniques that require dexterity and grip strength to maintain the folded shape and requires the user to insert their fingers into the vagina. It is difficult to perform insertion with existing cups, particularly for individuals with loss of dexterity or grip strength. Further, for proper functioning without leakage, the cup must be completely unfolded within the vagina, however, existing menstrual cups often do not completely unfold under their own mechanical spring forces and require a user to reach further into the cavity to inspect the shape and if necessary manipulate the cup to complete the unfolding. If existing cups are not placed ideally within the body, the wearer may experience leakage and discomfort. Accordingly, improved methods of manufacture of menstrual cups can help to improve the overall design for insertion as well as include additional features that aid in the ultimate removal.

Embodiments of Overmolding

Figure 1:
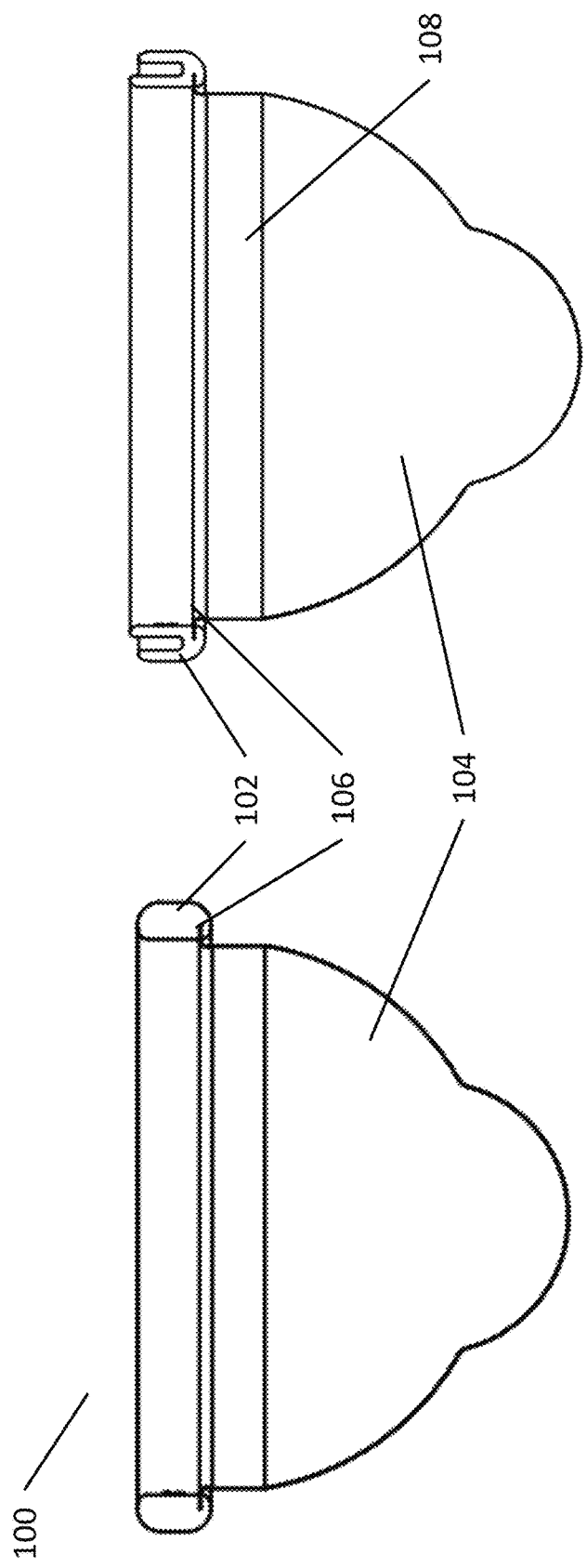
FIGS. 1A and 1B illustrates a cross sectional view of a menstrual device with an overmolded rim in accordance with several embodiments of the invention.

In accordance with many embodiments, menstrual cups may be manufactured using an overmolding technique. Overmolding involves a process of connecting two materials, similar or dissimilar, where an edge of a first material is overmolded by the second material. This process completely seals the edge of the first material within the cross section of the second material. FIGS. 1A and 1B illustrate a cross section of a menstrual cup 100 with an overmolded rim 102 in accordance with various 4 embodiments. As illustrated, the menstrual cup 100 has a catchment area or reservoir 104 that is located beneath the rim 102. The reservoir 104 has an edge 106 that is overmolded by the rim 102 of the menstrual cup. In accordance with many embodiments, the rim 102 completely encloses the edge 106 of the reservoir. Additionally, since many embodiments may use one or more materials in creating the menstrual cup 100, many embodiments may incorporate a transition region 108 within the reservoir portion 104 of the cup 100. The transition region 108 may be thicker than the main reservoir area but may also be thinner than the rim 102. In accordance with many embodiments, the transition area 108 may serve as a structural strengthening element as well as an additional resilient portion to aid in the insertion and deployment of the device. Although certain configurations of the overmolded edge 106 are shown it should be understood that the edge 106 may take on any configuration that is suitable for the overall functionality of the cup 100.

Figure 2:
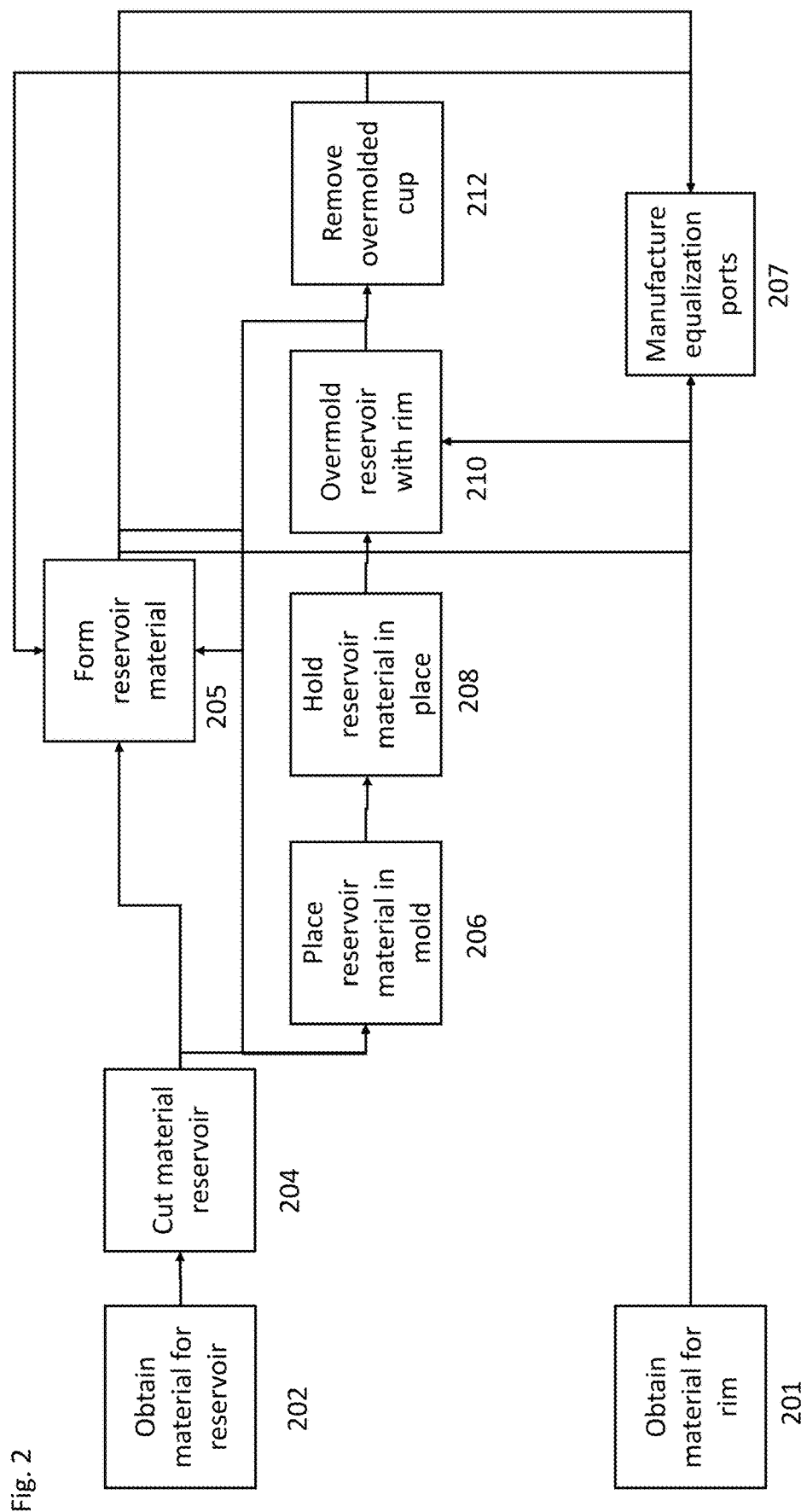
FIG. 2 illustrates a flow diagram of an overmolding process in accordance with several embodiments of the invention.

Many manufactures follow a more traditional approach to producing menstrual cups such as injection molding. While injection molding techniques can be used, many embodiments may utilize an alternative method of manufacture as illustrated by the flow diagram in FIG. 2. In accordance with various embodiments, a menstrual cup can be manufactured utilizing an overmolding technique where the material for the rim and the reservoir portions can be obtained or supplied (201 and 202). It can be appreciated that the material for each portion of the cup can be obtained simultaneously and form a variety of sources since various embodiments may include one or more different materials in either the rim or the reservoir or both. In some embodiments, the material may be the same material. Accordingly, it can be appreciated that parallel processes for the different components can be implemented in accordance with some embodiments. In accordance with many embodiments, the reservoir material can be cut (204) to a desired shape or to a shape that can be formed into the end product. For example, some embodiments may have larger reservoirs than others and may require a larger material blank than others.

Material blanks can be cut (204) in any number of ways such that the reservoir material is cut to the desired dimensions that correspond to the rim. For example, the reservoir material can be cut (204) by die cutting, laser cutting, preforming, etc. Additionally, many embodiments may utilize a variety of materials for both the rim portion as well as the reservoir portion. For example, the materials for either the rim or reservoir may be selected from any suitable material such as bio-based material, biodegradable material, medical grade silicone, plastic (food grade or otherwise), etc. Additionally, either the rim or the reservoir or both may be made of one or more materials.

Once the materials have been selected (201 and 202), cut (204), and/or pre-processed (if needed) the shaped reservoir material can then be prepared for molding the rim by installing it into a molding device (206). Some embodiments may incorporate a holding step (208) that holds the reservoir material in place during processing. Such methods may include vacuum, adhesive, clamping, or a combination thereof. In some embodiments the reservoir material may be pre-formed (205) in a parallel process. Accordingly, the pre-formed reservoir can conform to the mold for overmolding the edge such that it has predefined end shape. Whether preformed or molded into shape after the overmolding process, the material will still need to be held in a mold for overmolding, in accordance with numerous embodiments. With the reservoir material in place, the rim can then be molded around the outer edge of the reservoir material (210) such that the edge is completely enclosed within the molded rim of the cup. Once the rim has been overmolded on the edge of the reservoir material (210), the reservoir can be formed, either in the mold or in a separate step if needed, and the finished product can be removed from the mold (212) and prepared further for packaging. When forming the reservoir in the mold (205), specialized heating can be applied to selectively heat the reservoir material while avoiding heating the mold. Heating methods to do this include rapid resistive heating, infrared heating coupled to absorbent pigments or coatings applied to the reservoir material, and hot gas used to pressurize the forming chamber and heat the reservoir at the same time. In accordance with some embodiments, the rim may be configured with air equalization ports (207) for improved removal. The ports can be used to aid in removal of the cup in a number of different ways which will be described in greater detail further below with respect to FIGS. 9A-9H. However, in many embodiments the equalization ports may be formed during or after the molding process.

In accordance with many embodiments, the overmolding of the rim and reservoir can be an important part of the development and manufacture process to help improve sustainability of the cup. The overmolding process allows for a wider range of material combinations to be used. Although certain configurations and processing steps are described herein with respect to manufacturing of a menstrual cup, it should be understood that the any combination of process steps and/or materials can be used together or separately in accordance with the various embodiments.

Embodiments of a Menstrual Cup

Figure 3:
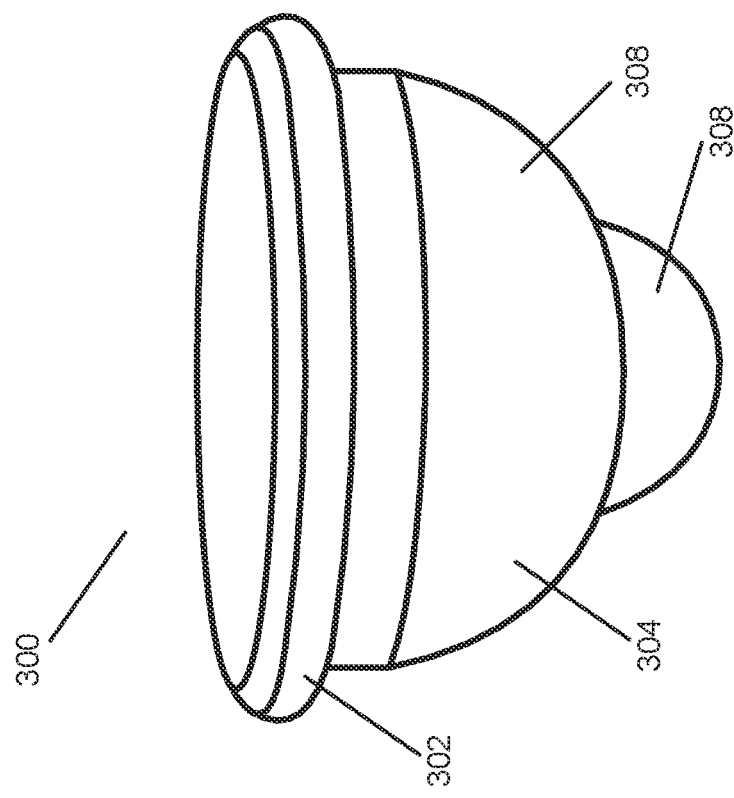
FIG. 3 illustrates a menstrual device in accordance with several embodiments of the invention.

In accordance with many embodiments, the overmolding of the rim and reservoir can be an important part of the development and manufacturing process to help improve usability of the cup. Additionally, many embodiments may incorporate one or more designs into the cross section of the rim as well as the reservoir that can provide for an improved functionality of the cup. For example, FIG. 3 illustrates a menstrual cup 300 with a multi-level rim 302 and a reservoir 304 with an upper wide portion 306 and a lower portion 308 with a smaller diameter than the upper portion. The multiple levels or transitions of the rim 302 can provide for improved insertion and removal of the cup/disc by providing more of a contoured surfaced that will not interfere with the body of the user. Additionally, the step 310 can function as a seal against the walls of the vagina while the cup is inserted. It can be appreciated that the rim and step 310 can be made of the same material or can be made of different materials or can be made of materials with different physical properties. For example, as many cups have a resilient rim the rim 302 and the step can be made of materials that differ in durometer so as to maintain the resiliency of the cup as well as improve the comfort for the user.

Figure 4:
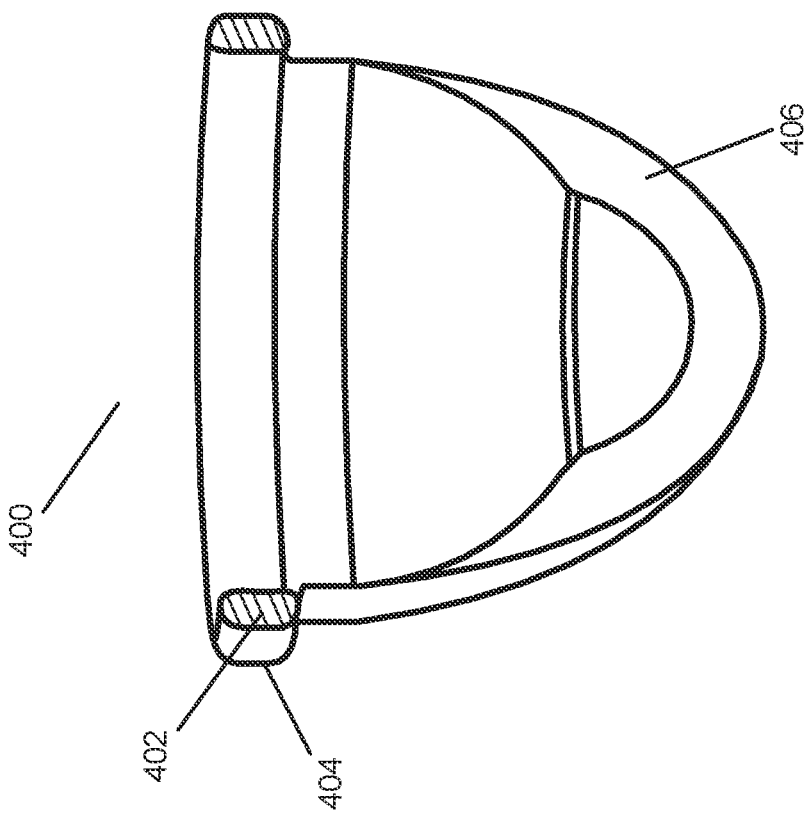
FIG. 4 illustrates a cross sectional view of a menstrual device in accordance with several embodiments of the invention.

FIG. 4 illustrates a cross section of a menstrual cup 400 with a rim 402 that has a half circular cross section in accordance to some embodiments. In some embodiments the rim 402 may have small ridges or textures 404 that can aid in handling or gripping of the cup. Adding textured features to the rim 402 can aid in the insertion of the cup, especially for individuals who may have dexterity problems. Additionally, some embodiments may have larger reservoirs 406 where the reservoir has a tapering cross section the provides for greater volume and catchment capabilities. In accordance with many embodiments, the edge cross section as well as the reservoir can be tunable or adjustable to fit the needs of any number of users. For example, some embodiments can have more shallow reservoirs while others have deeper larger reservoirs. Accordingly, many embodiments may have reservoirs that range in volume from 25-75 ml. As can be appreciated, the adjustability of the rim and the reservoir can help to improve applicability to the end user as no one person is the same.

The overall functionality and comfort of any menstrual device is important from a user standpoint. Furthermore, since no one user is the same, having a number of different functional and comfort elements can be important to a number of users. Accordingly, many embodiments may be adapted to improve the functionality of the cup as well as improve comfort for the user. One key aspect that relates to comfort and usability is the rim design. This is generally because the rim is the main component of the cup that interacts with the user during insertion, removal, and use. The rim contacts the side walls of the vagina as well as is designed to direct the flow of fluid into the reservoir and prevent unwanted leaks. FIGS. 5A through 8 illustrate menstrual cups with various types of rim designs to help improve comfort and usability in accordance with various embodiments.

Figure 5C:
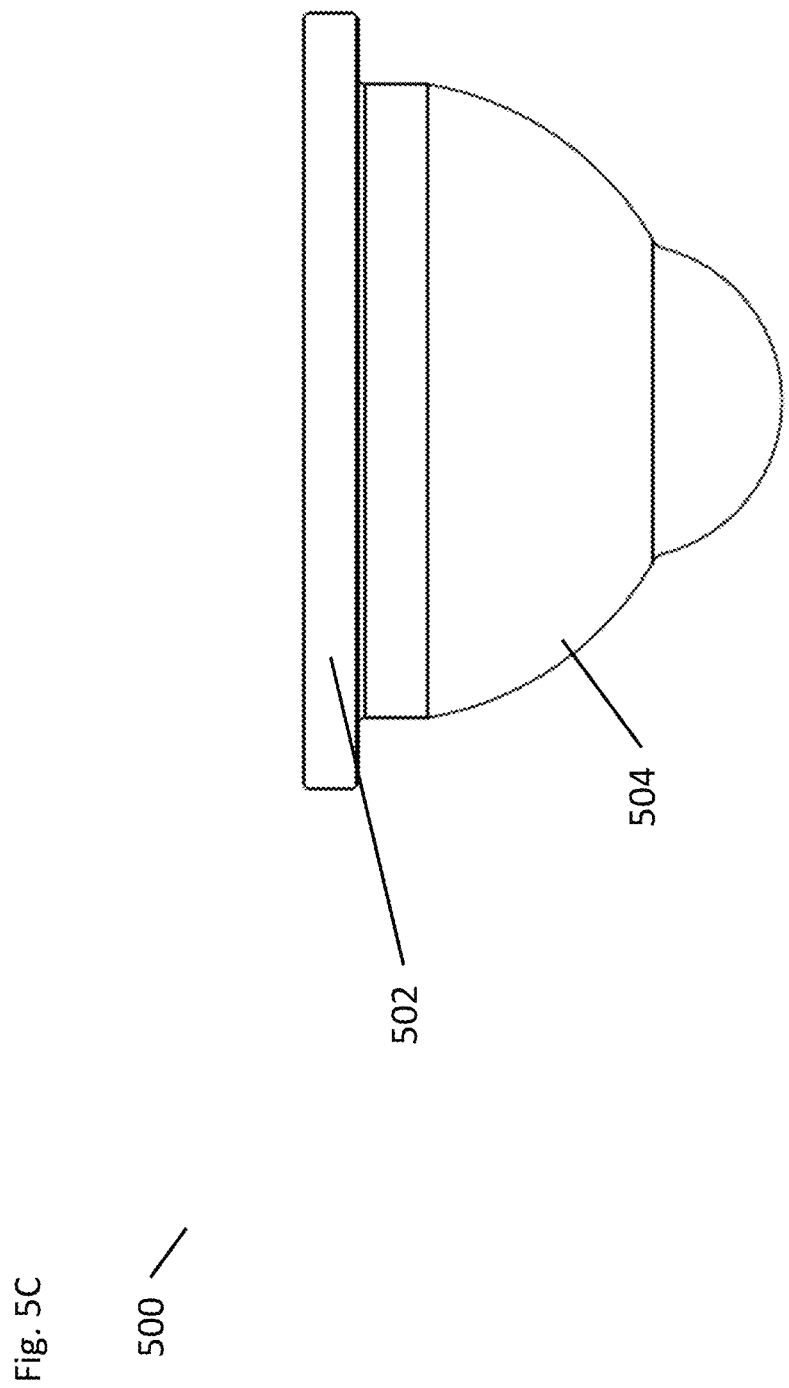

FIGS. 5A through 5C illustrate an embodiments of a menstrual cup 500 with a rim element 502 extends outwardly from the catchment portion 504 of the cup 500. In a number of embodiments, the rim may have a number of resilient support elements 506 that extend outward from the main body 508 of the rim and are interconnected by an outer resiliently flexible rim 510. Additionally, each of the resilient support element 506 are spaced apart such that the movement of each of the elements 506 does not interfere with the movement of adjacent elements. In some embodiments, the elements 506 can be positioned at an angle, such as a helical angle, in relation a surface of the rim. In various embodiments, the elements 605 can be configured to fold over onto an adjacent element during the exposure to an outward force. Such configurations, with resilient elements can allow for flexibility and adjustability within the rim such that usability is improved among a variety of users. In numerous embodiments the spaces 512 between the elements 506 can extend through the thickness of the rim. One objective of such structural configurations is to allow for the locational stiffness of the cup to be tuned to the various contact and non-contact surfaces. For example, many embodiments may use more compliant materials and/or configurations of materials in in areas or edges of the cup that would be considered "body contacting." In contrast, in some embodiments, more rigid and stiff structure and/or material combinations can be used to provide mechanical resiliency in non-body contact areas. Additionally, due to the variability that may be required, it can be appreciated that many embodiments may vary the structure and/or material configurations in more than one dimension. In other words, the variability can occur in the X, Y, and Z planes of any given design. Furthermore, it can be appreciated that any number of manufacturing methods can be used, including but not limited to additive manufacturing, injection molding, overmolding etc.

Figure 6A:
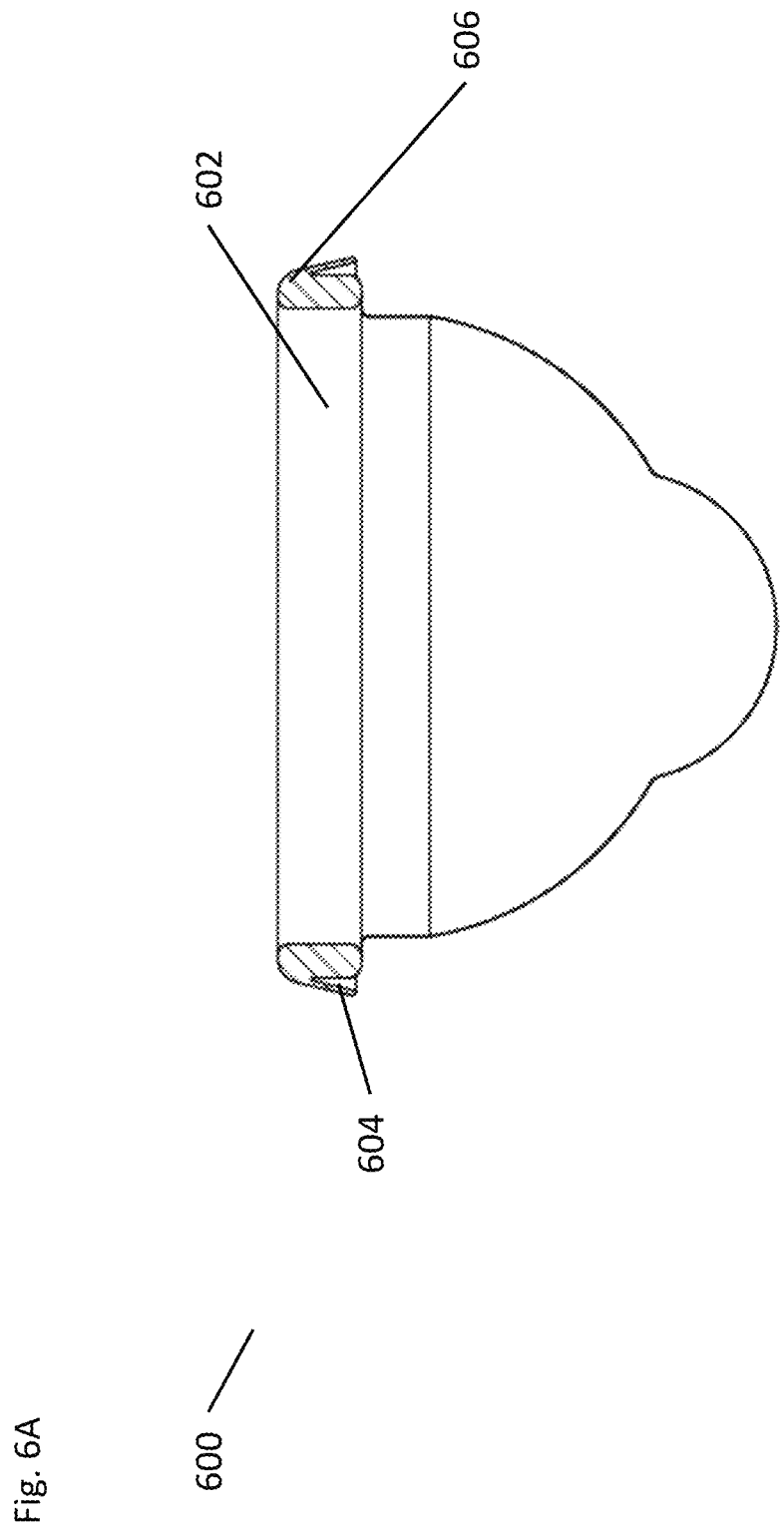

FIGS. 6A through 6C, for example, illustrates a menstrual cup 600 with a rim 602 that has an outward seal or sweep 604 disposed circumferentially on the outer surface of the rim 602. The sweep, in numerous embodiments, can be positioned at a downward angle sweeping downward and outward away from the main body of the rim 602. This can improve the overall insertion angle of the cup as well as offer a seal against the walls of the vagina. In many embodiments, the sweep can be made of a resiliently compliant material that moves or complies with the user as well as provides support and structure. In accordance with many embodiments, the sweep may be molded into the rim during a molding process similar to those described above. The sweep may also be attached by some other process such as heat welding or bonding. The sweep 604, in accordance with some embodiments, can provide for a more compliant outer surface of the rim 602 such that the seal of the cup is maintained during use. Numerous embodiments may have a rim 602 where the leading edge 606 is curved or contoured in some fashion to improve the transition between the rim and the sweep 604. The leading edge, generally refers to the upper edges of the rim of a cup that is inserted first into the vaginal canal toward the cervix. Accordingly, it can be advantageous to have the leading edge of a cup that is configured in such a manner so as to distribute the forces that occur against the rim during insertion and use. As such many embodiments may have rim designs that are configured with contoured or chamfered leading edges.

Figure 7D:
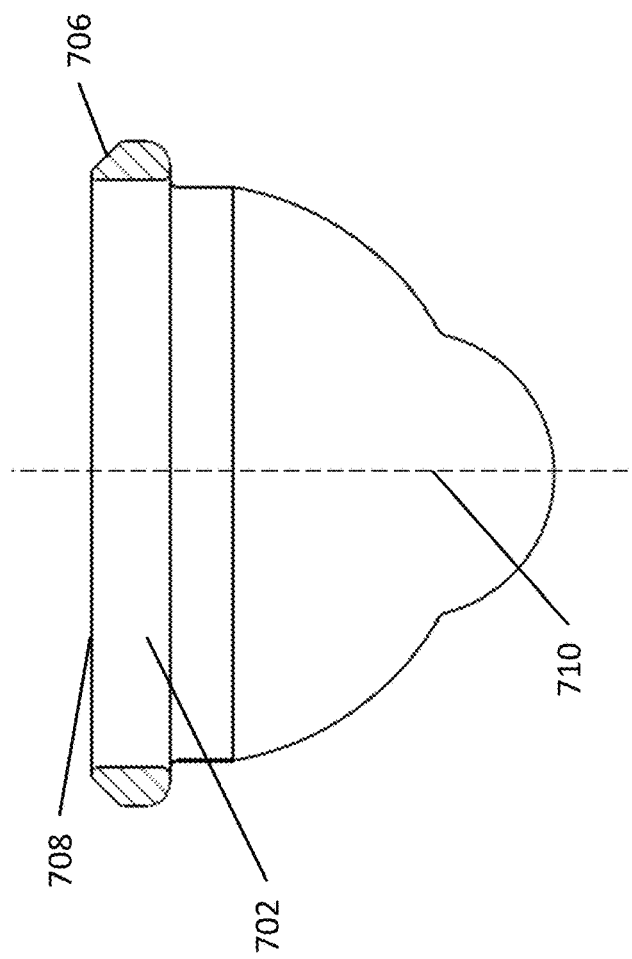
Figure 7C:
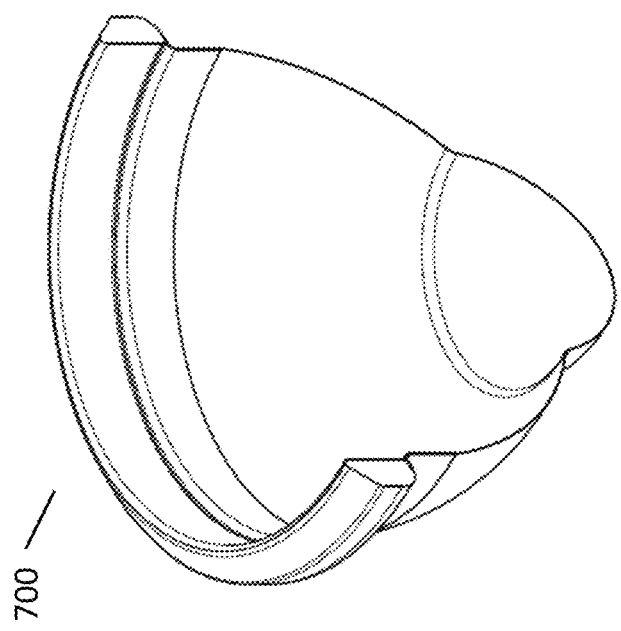
Figure 7E:
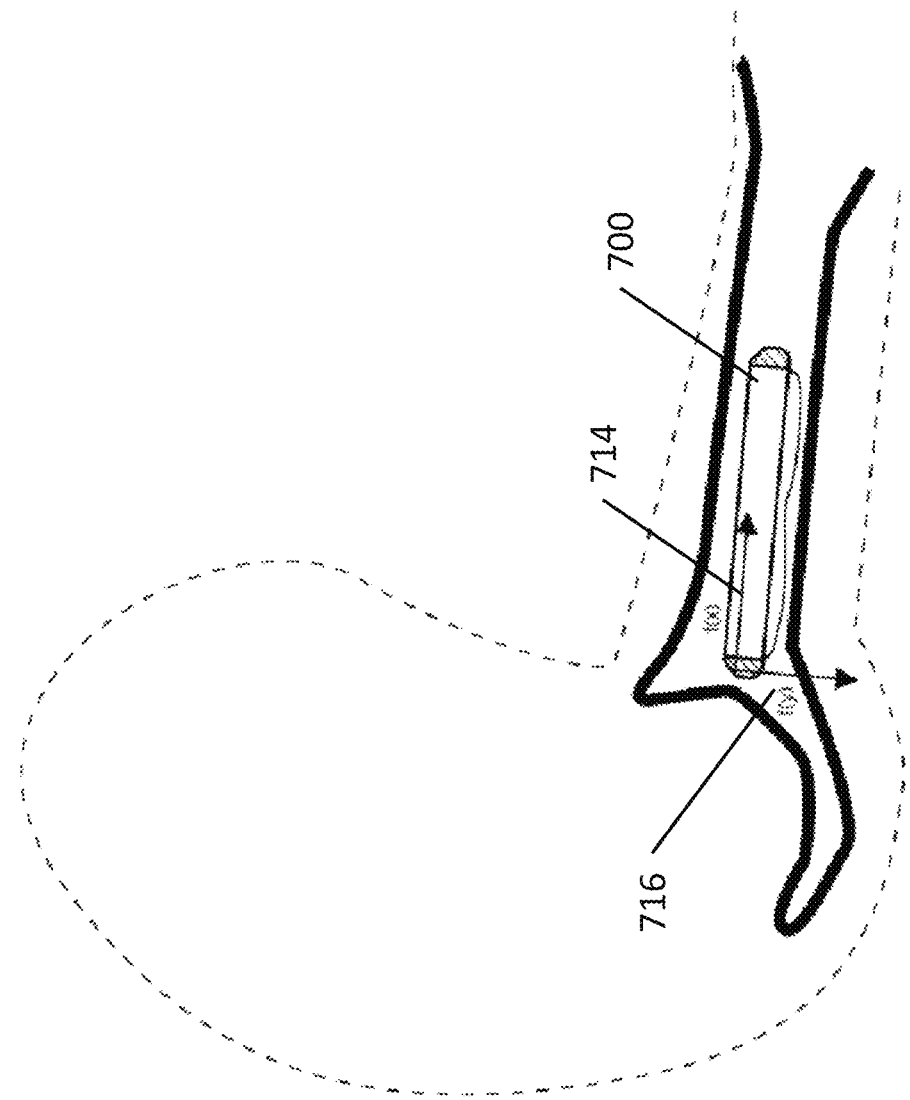

FIGS. 7A through 7E illustrate various views of an exemplary embodiment of a cup 700 with a rim portion 702 that has a specifically contoured leading edge 704. The leading edge 704 in accordance with many embodiments is contoured with a chamfer or a slope 706 such that the slope 706 is at an off axis angle that slopes downward away from a top portion 708 of the rim. Having a slope at the leading edge can distribute the unilateral force against the rim in proportion to the angle of the slope an in a direction normal to the sloping edge 706. In other words, as the unilateral force from the vaginal walls or cervix interacts with the sloping edge 706 a rotating motion can be generated and help move the cup 700 in a direction parallel to the central axis of the cup 710. This can help to facilitate movement of the cup advancing beyond the cervix, thus placing it in the correct position in the fornix. For example, FIG. 7E illustrates a menstrual cup and/or disc in the initial position before the final position. The cup 700 has a force in the X direction 714 that results in a force and/or movement in the Y direction 716 due to the force on the chamfered portion of the rim. This can be very advantageous in that numerous users can suffer from dexterity issues that can limit their ability to properly insert the cup 700. As can be appreciated the slope 706 can be of any angle that is suitable to create the desired movement of the cup against the unilateral forces applied. Some embodiments may use a 45° angle, however many embodiments can use smaller or larger angles.

It can be appreciated that the rim of any embodiment of a cup may take on any number of cross sections that can improve the overall functionality and comfort of the cup. Various cross sections may provide graspable surfaces and thereby aid in interfacing with insertion or removal tools. For example, FIG. 8 illustrates a table with various cross sections of rims and the associated volume of material. Accordingly, it can be seen that the various cross sections can reduce the material used. This indicates that the cross section can be optimized for improved environmental impact as well as usability. In accordance with many embodiments, the cross section may be a dome shape, triangular shape, U-shaped, or any other suitable shape for manufacturing and use. Furthermore, in some embodiments the geometric dimensions can vary. In some embodiments the rim diameter can be between 2" and 3". In other embodiments, the height of the rim may be between 0.25" and 1". Likewise, the width of the rim may be between 0.25" and 1", in accordance with embodiments.

Figure 9A:
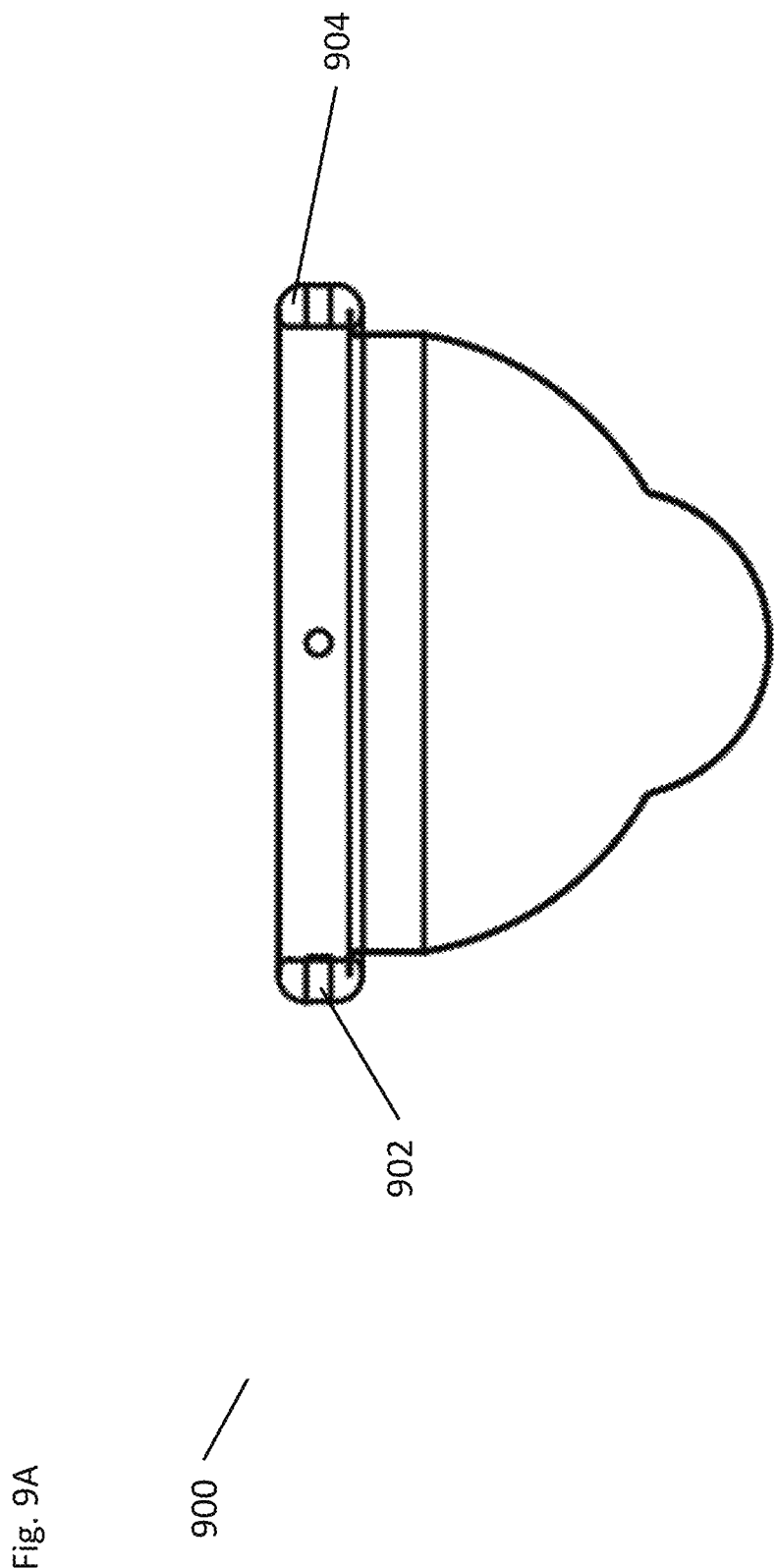

As can be appreciated the rim of the cup can serve a number of different functions, such as providing a resilient component to help with insertion, and provide a component that helps better direct the flow of fluid. Additionally, it can be appreciated that the rim, in many embodiments, serves as the key component for insertion and removal. Accordingly, many embodiments may incorporate one or more features within the rim of the cup that can improve the insertion and/or removal process and thus prevent unwanted spills or leaks that can often occur from more traditional designs. For example, FIGS. 9A through 9H, illustrate embodiments menstrual cups with removal/insertion enhancement features. FIG. 9A illustrates a menstrual cup 900 that incorporates channels 902 that pass through the body of the rim 904. These channels 902 can help to prevent unwanted suction that can occur with similar menstrual devices. Channels may also provide surfaces to aid in gripping the device by insertion or removal tools. Once a device is inserted properly, the rim can often time create a suction between the rim and the walls of the vagina. The suction can make the removal of such devices more difficult and can often lead to leaks and/or spills. Accordingly, some embodiments may use a number of channels 902 to help reduce or eliminate the suction and thus improve the removal process. FIG. 9B illustrates an isometric view of a menstrual cup 900 with horizontally configured channels 902. Although the channels 902 illustrated in FIGS. 9A and 9B pass through the thickness of the rim 904, it can be appreciated that channels can be configured to pass through the height or even at angles that are off axis.

Figure 9D:
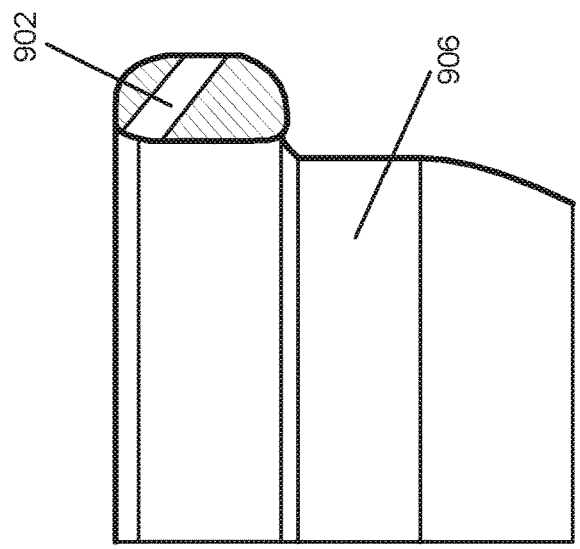
Figure 9C:
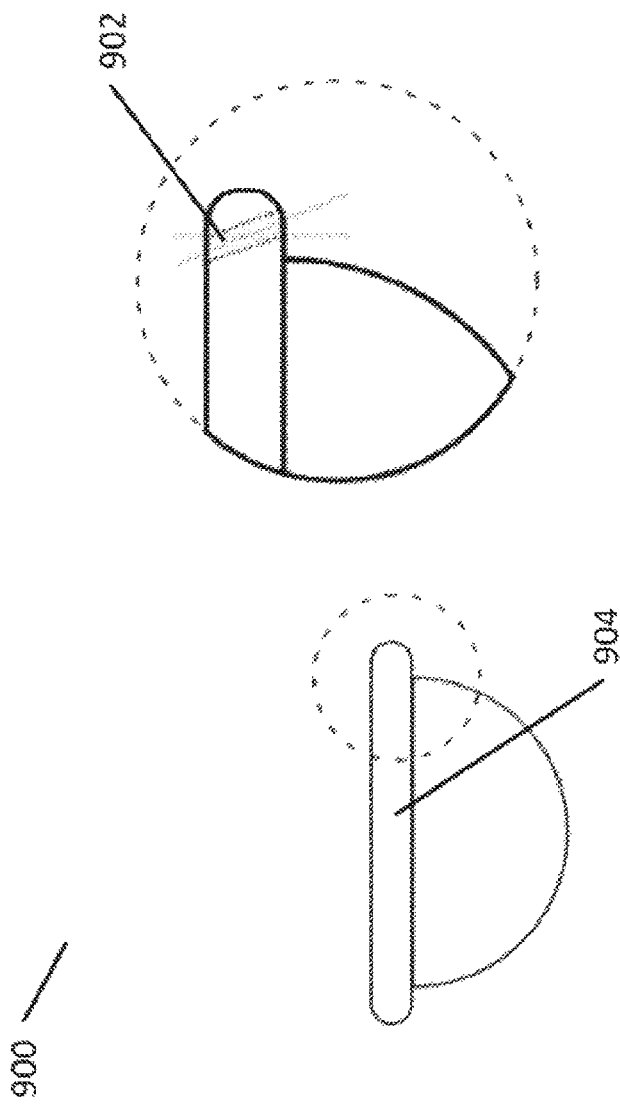
Figure 9E:
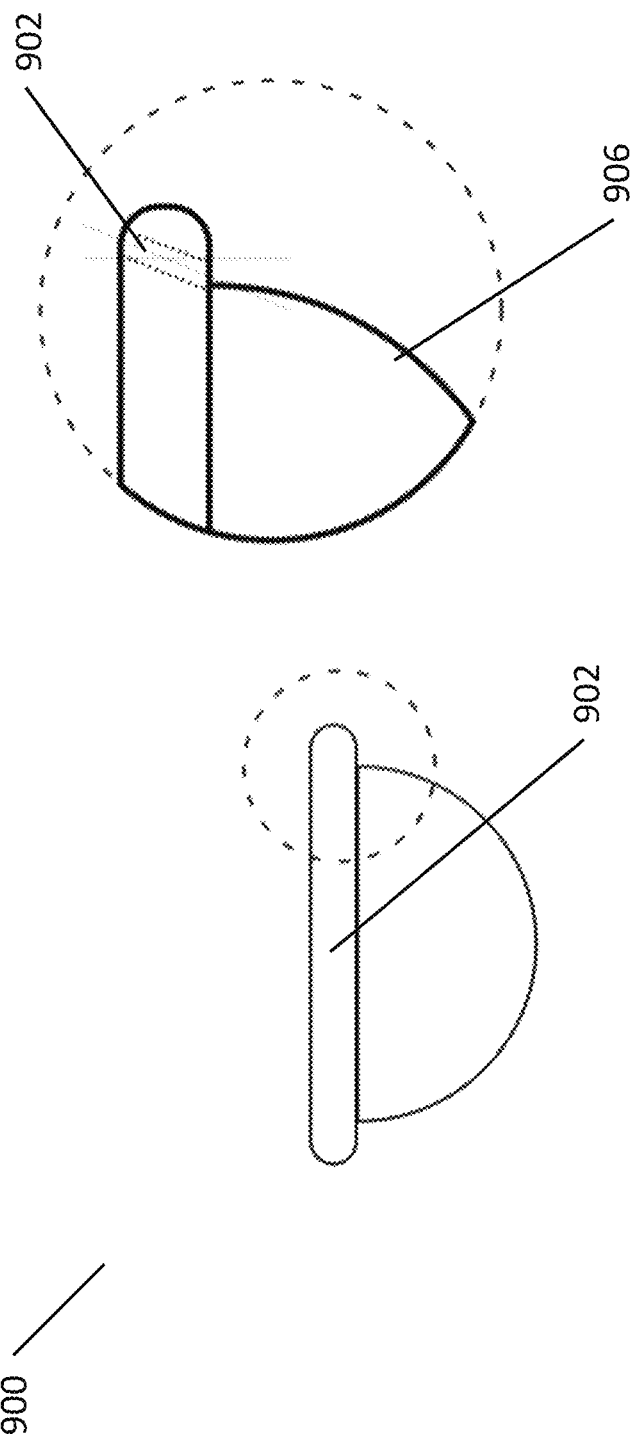

For example, FIGS. 9C through 9E illustrate a menstrual cup 900 with channels 902 that are configured to pass through the rim 904 at an angle that is off axis from the vertical. FIGS. 9C and 9D illustrate a channel 902 that is configured to slant away from the body of the cup 906 while FIG. 9E illustrates a channel that is configured to slant towards the body of the cup 906. Although the cross sectional views illustrate a single channel it can be appreciated that embodiments of a menstrual cup can incorporate one or more channels.

Figure 9F:
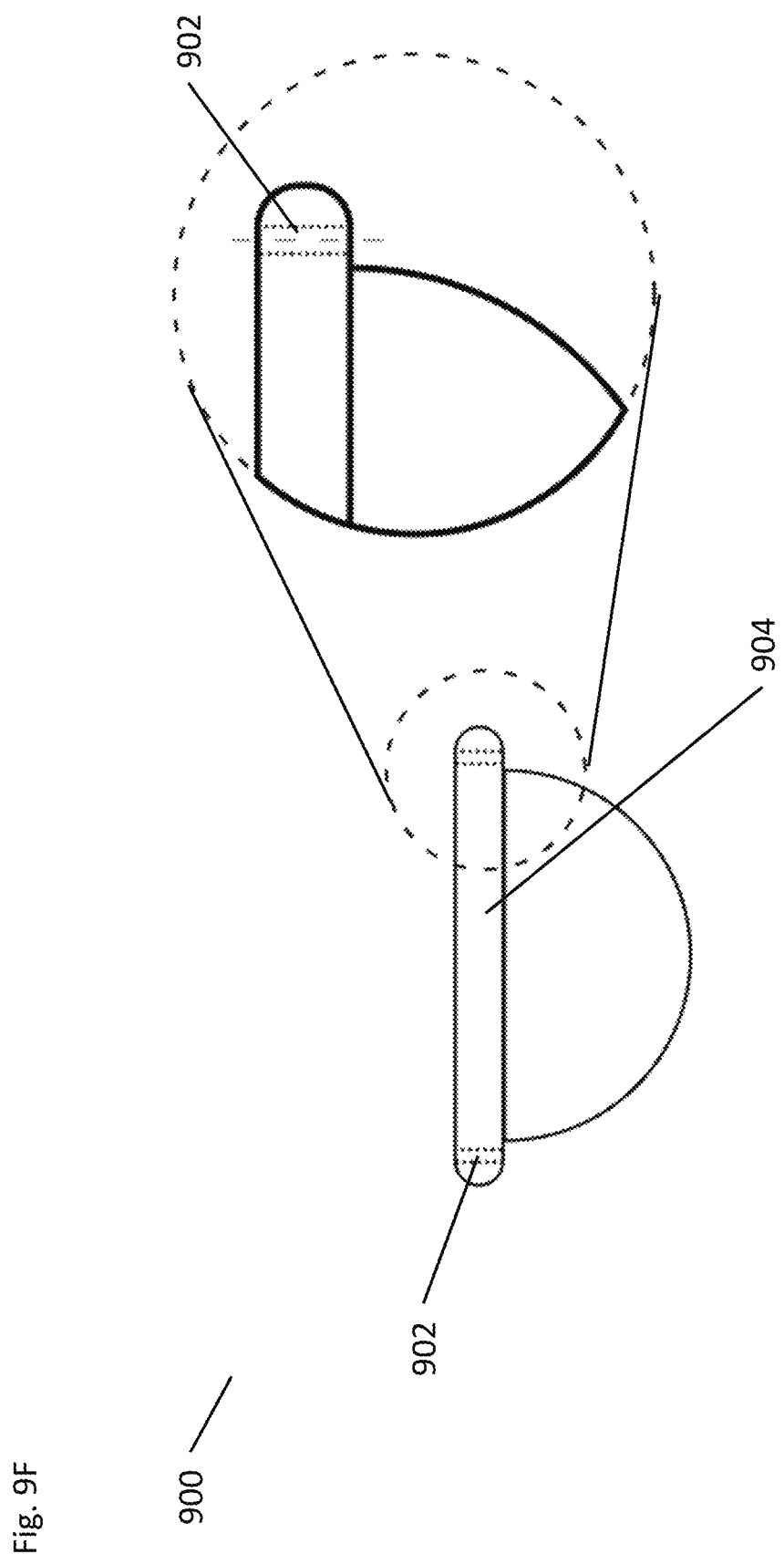

FIGS. 9F though 9G illustrate embodiments of a menstrual cup with vertically aligned channels in portions of the rim 904. For example, FIG. 9F illustrates an embodiment of a menstrual cup 900 with vertical channels 902 that run vertically through the body or height of the rim 904. The vertical channels, similar to horizontal ones, can help to reduce or remove unwanted suction and can also act as attachment points for a removal device. In some embodiments a removal device (not shown) can insert one or more connecting elements into the channels 905 to grab hold of the cup and remove it. Removal devices can be beneficial if the user suffers from dexterity issues that make it difficult to remove. Likewise, insertion devices can be used in a similar manner.

Figure 9G:
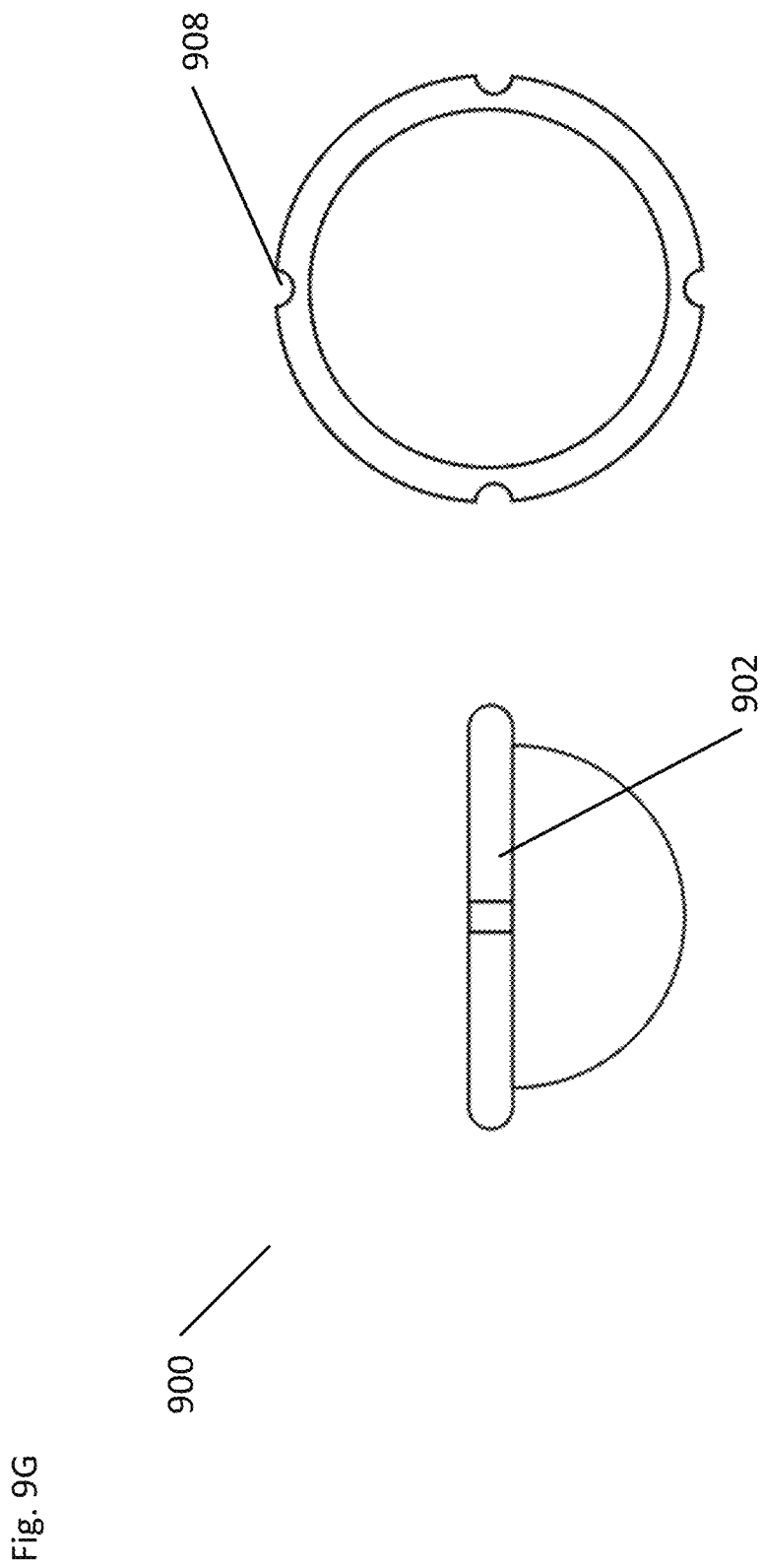
Figure 9H:
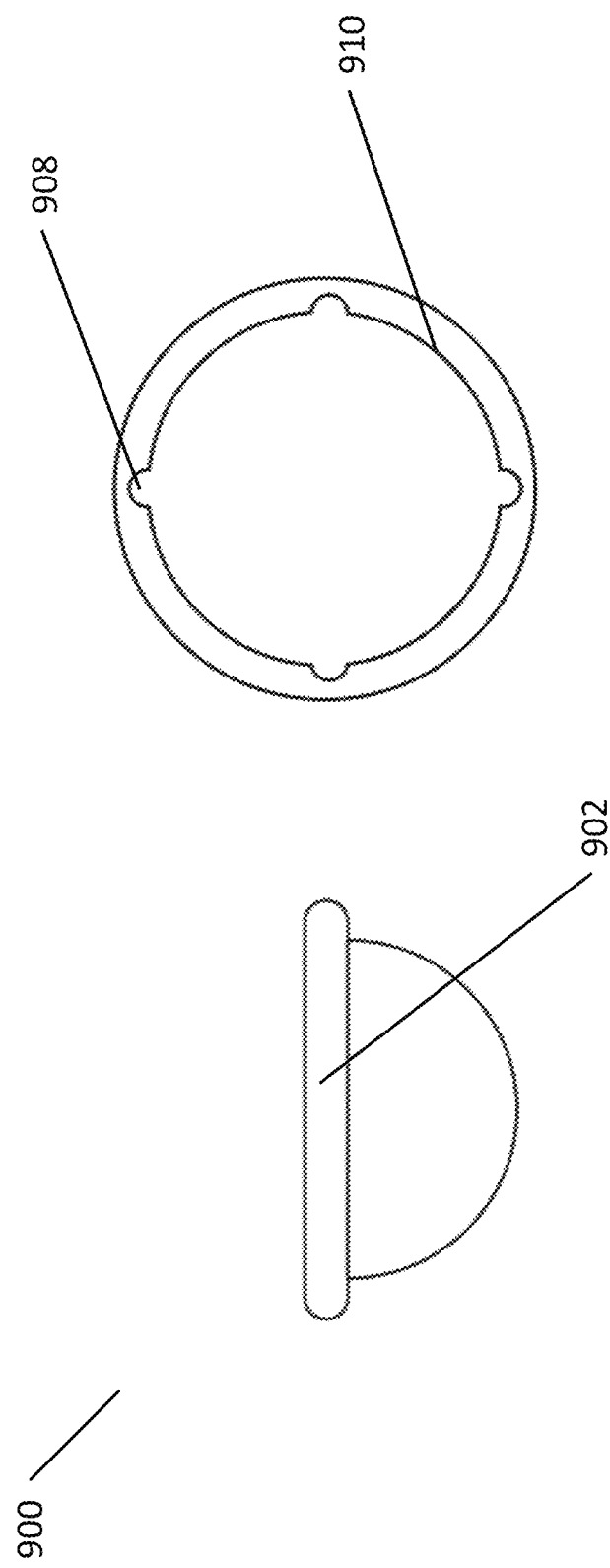

Similarly, FIG. 9G illustrates vertically aligned channels 905 in the rim that pass through a portion of the rim leaving a cut out section 908. In some embodiments, channel can have a "C" shaped cross section. The "C" shaped channels 908 can be positioned in any number of locations and can act in a similar manner to other channels described herein. Additionally, it can be appreciated that the channel cut outs 908 can have any number of cross section and are not limited to a "C" shape. Likewise, the cutout channels 908 can be configured to be at a number of different off axis angles. Similar to the cutout channels illustrated in FIG. 9G, FIG. 9H illustrates cutout channels 908 that are disposed on an internal surface 910 of the rim. Although certain embodiments are shown, it should be understood that any number of channels may be used and a variety of different cross sections of channels may be used within the same rim of a cup. Additionally, many embodiments may place the channels in any number of locations including through a sweep or seal or compliant portion (as shown in FIGS. 5 and 6).

Although certain components and configurations of a menstrual cup are illustrated, it should be understood that any number of components and configurations can be used together or separately in accordance with embodiments of the invention.

Figure 10B:
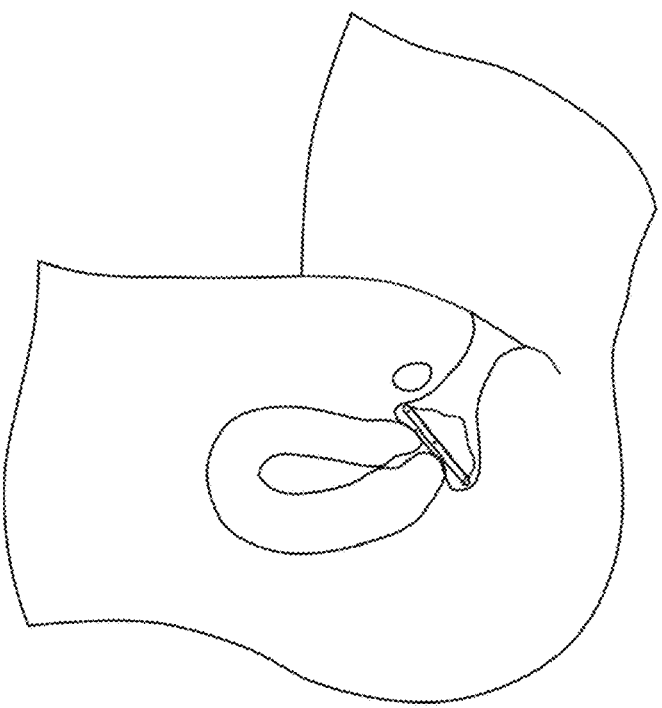
FIGS. 10A and 10B illustrate insertion and removal of a menstrual device in accordance with several embodiments of the invention.
Figure 10A:
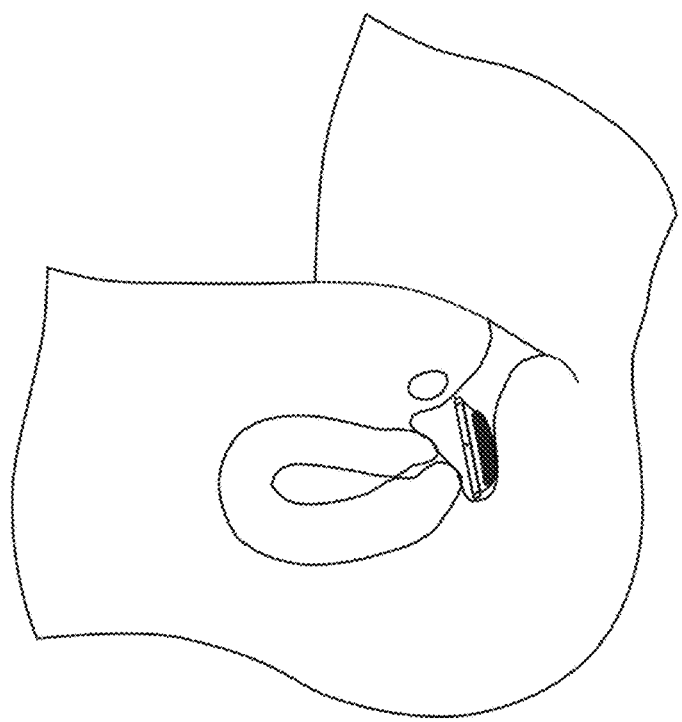

In reference to usability, FIGS. 10A and 10B illustrate an embodiment of a cup during insertion (10A) and removal (10B). It should be understood that any embodiment described herein may be used to help improve the insertion and removal of the cup. Therefore the overall user experience may be greatly improved.

DOCTRINE OF EQUIVALENTS

As can be inferred from the above discussion, the above-mentioned concepts can be implemented in a variety of arrangements in accordance with embodiments of the invention. Specifically, menstrual cups with improved rim designs that aid in the insertion and removal of the cup as well as improve the environmental impact are illustrated. Achieving such functionality, according to embodiments, involves the implementation of special arrangements/designs between subsystems described above, and their equivalents.

Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:
1. A menstrual device comprising:
    a body portion being made of a first material of a first durometer and defining a generally circular shape with an interior surface defining a reservoir; and
    a resiliently foldable rim connected to the body portion and being made of a second material having a second durometer, wherein the second durometer is higher than the first durometer.
2. The menstrual device of claim 1, wherein the first material is silicone, and the second material is silicone.

3. The menstrual device of claim 1, wherein the resiliently foldable rim is molded onto the body portion such that the resiliently foldable rim encloses an upper edge of the body portion.

4. The menstrual device of claim 1, wherein the resiliently foldable rim has a cross section selected from a group consisting of triangular, half circular, and U shaped.

5. The menstrual device of claim 1, wherein the reservoir has a volume ranging from 25 ml to 75 ml.

* * * * *